US011576609B2

(12) United States Patent
Jiang et al.

(10) Patent No.: US 11,576,609 B2
(45) Date of Patent: Feb. 14, 2023

(54) NONINVASIVE METHODS FOR DETECTING LIVER FIBROSIS

(71) Applicant: GEORGIA STATE UNIVERSITY RESEARCH FOUNDATION, INC., Atlanta, GA (US)

(72) Inventors: Yi Jiang, Atlanta, GA (US); Hao Chen, Atlanta, GA (US); Bin Zhang, Atlanta, GA (US); Sergey Klimov, Atlanta, GA (US)

(73) Assignee: Georgia State University Research Foundation, Inc., Atlanta, GA (US)

( * ) Notice: Subject to any disclaimer, the term of this patent is extended or adjusted under 35 U.S.C. 154(b) by 514 days.

(21) Appl. No.: 16/627,033

(22) PCT Filed: Jun. 29, 2018

(86) PCT No.: PCT/US2018/040198
§ 371 (c)(1),
(2) Date: Dec. 27, 2019

(87) PCT Pub. No.: WO2019/006248
PCT Pub. Date: Jan. 3, 2019

(65) Prior Publication Data
US 2020/0121240 A1 Apr. 23, 2020

Related U.S. Application Data

(60) Provisional application No. 62/527,469, filed on Jun. 30, 2017.

(51) Int. Cl.
*A61B 5/00* (2006.01)
*A61B 5/024* (2006.01)
(Continued)

(52) U.S. Cl.
CPC ............ *A61B 5/4244* (2013.01); *A61B 5/024* (2013.01); *A61B 5/4842* (2013.01);
(Continued)

(58) Field of Classification Search
CPC ..... A61B 5/4244; A61B 5/024; A61B 5/4842; A61B 5/4848; A61B 8/06; A61B 8/488; A61B 8/5223; A61B 8/08; G16H 50/30
See application file for complete search history.

(56) References Cited

U.S. PATENT DOCUMENTS 4,327,739 A   4/1982 Chmiel et al.
5,425,365 A   6/1995 Iinuma
(Continued)

FOREIGN PATENT DOCUMENTS

CN   2728423 A   9/2005
CN   1871010 A   11/2006
(Continued)

OTHER PUBLICATIONS

Chen Xiao-Rong, et al. "Portal hemodynamics in patients with different syndromes of cirrhosis", Journal of Chinese Integrative Medicine. May 2004, vol. 2, No. 3, May 2004 (May 2004), pp. 178-181.
(Continued)

*Primary Examiner* — Gary Jackson
*Assistant Examiner* — Sebastian X Lukjan
(74) *Attorney, Agent, or Firm* — Meunier Carlin & Curfman LLC

(57) ABSTRACT

The present disclosure relates to noninvasive methods for detecting liver fibrosis. Disclosed herein are noninvasive liver fibrosis detection methods that use Doppler Ultrasound devices and a physics-based machine learning method. Further disclosed herein are methods for detecting liver fibrosis in a subject by detecting and measuring the presence of a
(Continued)

shift in the frequency of blood flow in the hepatic vein as compared to the frequency of blood flow in the portal vein.

20 Claims, 7 Drawing Sheets

(51) Int. Cl.
    *A61B 8/06* (2006.01)
    *A61B 8/08* (2006.01)
(52) U.S. Cl.
    CPC .............. *A61B 5/4848* (2013.01); *A61B 8/06* (2013.01); *A61B 8/488* (2013.01)

(56) References Cited

U.S. PATENT DOCUMENTS

| | | |
|---|---|---|
| 2007/0004744 A1 | 1/2007 | Kreisel et al. |
| 2012/0271166 A1 | 10/2012 | Shao et al. |
| 2015/0148671 A1 | 5/2015 | Chen et al. |
| 2016/0020666 A1 | 7/2016 | Fraser et al. |
| 2019/0117094 A1 | 4/2019 | Qi |

FOREIGN PATENT DOCUMENTS

| | | |
|---|---|---|
| CN | 101699280 A | 4/2010 |
| CN | 101779966 A | 7/2010 |
| CN | 102421372 A | 4/2012 |
| CN | 103637821 A | 3/2014 |
| CN | 105452857 A | 3/2016 |
| CN | 105574861 A | 5/2016 |
| CN | 105825070 A | 8/2016 |
| RU | 2422091 C1 * | 6/2011 |
| RU | 2422091 C1 | 6/2011 |
| TW | 201338760 A | 10/2013 |
| TW | 201519872 A | 6/2015 |
| WO | 2010131136 A1 | 11/2010 |
| WO | 2012/011872 A1 | 1/2012 |
| WO | 2014075082 A1 | 5/2014 |
| WO | 2016/008014 A1 | 1/2016 |

OTHER PUBLICATIONS

Supplementary European Search Report issued in EP 18822808, dated Feb. 25, 2021, 8 pages.

Balasubramanian et al. "Assessment of Portal Venous and Hepatic Artery Haemodynamic Variation in Non-Alcoholic Fatty Liver Disease (NAFLD) Patients," Journal of Clinical and Diagnostic Research, Aug. 1, 2016 (Aug. 1, 2016), vol. 10, Iss. 8.

Bang et al. "Doppler ultrasonography measurement of hepatic hemodynamics during Valsaiva maneuver: healthy volunteer study," Ultrasonography, Aug. 27, 2014 (Aug. 27, 2014), vol. 34, Iss. 1.

Khalid, G.A "The Effect of Doppler Phenomenon on the Speed of Blood Flow," Al-Khwarismi Engineering Journal, Dec. 31, 2012 (Dec. 31, 2012), vol. 8, No. 4.

Leao et al. "Non-Invasive Assessment of Fibrosis Using Color Doppler Ultrasound in Patients with Hepatitis C Virus in the Amazon Rainforest, Brazil," The American Journal of Tropical Medicine and Hygine, Feb. 1, 2012 (Feb. 1, 2012), vol. 86, Iss. 2.

Mahajan et al. "Diagnostic Value of Doppler Ultrasonography in Non-invasive Diagnosis of Chronic Liver Disease and Portal Hypertension," International Journal of Anatomy Radiology and Surgery, Dec. 31, 2016 (Dec. 31, 2016), vol. 5, Iss. 4.

Stankovic et al. "Normal and Altered Three-dimensional Portal Venous Hemodynamics in Patients with Liver Cirrhosis," Radiology, Mar. 1, 2012 (Mar. 1, 2012), vol. 262, Iss. 3.

International Search Report and Written Opinion in corresponding PCT Application No. PCT/US2018/040198, dated Sep. 18, 2018, 10 pages.

Schuppan, Detlef, and Nezam H. Afdhal. "Liver cirrhosis." The Lancet 371.9615 (2008): 838-851.

Xu, Jan, et al. "Amyloid-β peptides are cytotoxic to oligodendrocytes." Journal of Neuroscience 21.1 (2001): RC118-RC118.

Falenski, Jessica A., Ulla Im Gerling, and Beate Koksch. "Multiple glycosylation of de novo designed α-helical coiled coil peptides." Bioorganic & medicinal chemistry 18.11 (2010): 3703-3706.

Alempijevic, Tamara, et al. "Doppler ultrasonography combined with transient elastography improves the non-invasive assessment of fibrosis in patients with chronic liver diseases." Medical ultrasonography 19.1 (2017): 7-15.

International Preliminary Report on Patentability issued for Application No. PCT/US2018/040198, dated Jan. 16, 2020.

Office Action, dated Jun. 8, 2022, received in connection with corresponding CN Patent Application No. 201880030162.6 (and English translation).

Search Report, dated May 26, 2022, received in connection with corresponding CN Patent Application No. 201880030162.6.

* cited by examiner

NONINVASIVE METHODS FOR DETECTING LIVER FIBROSIS

CROSS-REFERENCE TO RELATED APPLICATIONS

This application is a national stage application filed under 35 U.S.C. § 371 of PCT International Application No. PCT/US2018/040198, filed Jun. 29, 2018, which claims the benefit of U.S. Provisional Application No. 62/527,469, filed Jun. 30, 2017, which are hereby incorporated herein by reference in their entirety.

FIELD

The present disclosure relates to noninvasive methods for detecting liver fibrosis.

BACKGROUND

Liver fibrosis results from chronic damage to the liver, including hepatitis B and hepatitis C, alcoholic liver diseases, nonalcoholic fatty liver disease (NAFLD), and autoimmune hepatitis. As liver fibrosis progresses, the excessive accumulation of extracellular matrix proteins results in increased liver stiffness, leading liver cirrhosis, liver failure, and liver cancer.

According to the Centers for Disease Control and Prevention (CDC), cirrhosis and chronic liver disease are a major cause of death for men and women in the United States, killing approximately 38,000 people each year. In the United States, ~3.2 million are chronically infected with hepatitis C, with an estimated 8,000 to 10,000 deaths annually; 19,000 annual deaths from alcohol related liver diseases. In addition, China has a high-risk population of 300 million for liver fibrosis, including more than 100 million hepatitis B and C virus carriers and 200 million fatty liver patients. A conservative estimate of the number of new liver fibrosis patients in China is 4 to 8 million per year.

Liver fibrosis is serious, with a five-year transition rate of liver cirrhosis (Stage 4 liver fibrosis) to liver cancer of 6-15%, and the five-year mortality rate of liver cancer is greater than 90%. Liver cirrhosis is non-reversible, and thus it is extremely important to detect liver fibrosis when it is in the early stage. However, early stage liver fibrosis is asymptomatic. Therefore, in most cases, it is often too late for a patient with a liver disease (hepatitis and fatty liver) to even realize they have a liver fibrosis problem. In addition, current technologies only allow patients to do the test in large hospitals.

The current gold standard for detecting liver fibrosis is using an invasive needle biopsy, and relying on a pathologist's visual examination of the tissue images. Problems with needle biopsy include 1) low accuracy, which is due to both the large sampling error and the variability of pathologist's reading, and 2) pain and the potential medical risks (e.g. excessive bleeding) associated with the invasive procedure. A noninvasive technology also exists, which is an ultrasound device to measure the stiffness of liver based on elastography. This competing technology is in the form of a bulky and expensive device that are found in limited hospitals, with limited accuracy. The methods disclosed herein address these and other needs.

SUMMARY

Disclosed herein are new methods for detecting and diagnosing liver fibrosis. The invention herein improves upon the existing utility of the ultrasound process to provide for improved detection of liver fibrosis. Following on many years of research and development, the inventors have determined for the first time the relationship between Doppler Ultrasound frequency shift difference between the hepatic and portal veins and the stage of liver fibrosis.

While the methods used herein have used ultrasound technology, the methods have used ultrasound technology in an unconventional manner. For example, ultrasound technology is conventionally used for imaging organs or examining the development of a growing fetus. In contrast, as disclosed herein, the inventors applied the technology in an unconventional method using unconventional steps in order to detect liver fibrosis through noninvasive means.

The previous gold standard for detecting liver fibrosis included liver biopsy. This invasive biopsy method is painful, expensive, time-consuming, and offers low accuracy. Thus, the inventors used instrumentation that would not conventionally be used by doctors wanting to detect liver fibrosis. The use of Doppler Ultrasound in such an unconventional manner allows doctors to increase accuracy, while providing a noninvasive technology to the patient.

The noninvasive methods disclosed herein also alleviate the problem of undiagnosed early stage liver fibrosis detection by allowing patients to learn about their liver fibrosis stage in regular annual medical examinations that can be provided in hospitals and clinics at all levels. This technology can lower the cost and increase the convenience of examination by using standard ultrasound devices that are widely available. A large proportion of hospitals and clinics can offer these new methods for detecting liver fibrosis, thus allowing an increased number of patients to be tested and to determine their stage of liver fibrosis, and thus overcoming the existing difficulties in early-stage detection.

In one aspect, provided herein is a method for detecting liver fibrosis in a subject, comprising the steps: measuring the subject's heart beat rate; measuring frequency of blood flow by Doppler Ultrasound in a portal vein of the subject; measuring frequency of blood flow by Doppler Ultrasound in a hepatic vein of the subject; and determining the presence of a shift in the frequency of blood flow in the hepatic vein as compared to the frequency of blood flow in the portal vein; wherein an increase in the frequency of blood flow in the hepatic vein as compared to the frequency of blood flow in the portal vein is an indication of liver fibrosis.

In some embodiments, the frequency of blood flow is measured by Doppler Ultrasound in at least two locations in the hepatic vein of the subject. In some embodiments, the frequency of blood flow is measured by Doppler Ultrasound in three locations in the hepatic vein of the subject.

In some embodiments, the presence of a shift in the frequency of blood flow in the hepatic vein as compared to the frequency of blood flow in the portal vein of between about 0.0068 Hz and about 0.0200 Hz is an indication of stage 1 liver fibrosis. In some embodiments, the presence of a shift in the frequency of blood flow in the hepatic vein as compared to the frequency of blood flow in the portal vein of between 0.0068 Hz and 0.0200 Hz is an indication of stage 1 liver fibrosis.

In some embodiments, the presence of a shift in the frequency of blood flow in the hepatic vein as compared to the frequency of blood flow in the portal vein of between about 0.0200 Hz to about 0.0251 Hz is an indication of stage 2 liver fibrosis. In some embodiments, the presence of a shift in the frequency of blood flow in the hepatic vein as compared to the frequency of blood flow in the portal vein of between 0.0200 Hz to 0.0251 Hz is an indication of stage 2 liver fibrosis.

In some embodiments, the presence of a shift in the frequency of blood flow in the hepatic vein as compared to the frequency of blood flow in the portal vein of between about 0.0251 Hz to about 0.0401 Hz is an indication of stage 3 liver fibrosis. In some embodiments, the presence of a shift in the frequency of blood flow in the hepatic vein as compared to the frequency of blood flow in the portal vein of between 0.0251 Hz to 0.0401 Hz is an indication of stage 3 liver fibrosis.

In some embodiments, the presence of a shift in the frequency of blood flow in the hepatic vein as compared to the frequency of blood flow in the portal vein of greater than about 0.0401 Hz is an indication of stage 4 liver fibrosis (stage 4 liver fibrosis is also referred to as cirrhosis). In some embodiments, the presence of a shift in the frequency of blood flow in the hepatic vein as compared to the frequency of blood flow in the portal vein of greater than 0.0401 Hz is an indication of stage 4 liver fibrosis.

In some embodiments, the subject is treated with a therapeutic agent if the frequency of blood flow in the hepatic vein is increased as compared to the frequency of blood flow in the portal vein. In some embodiments, the therapeutic agent is selected from an antiviral agent, antibiotic, a diuretic, or a laxative.

In another aspect, disclosed herein is a method for detecting liver fibrosis in a subject, comprising the steps: measuring the subject's heart beat rate; measuring the frequency of blood flow in at least two locations in a subject's liver using a Doppler Ultrasound system; and determining a shift in frequency of blood flow between the at least two locations in the liver; wherein the shift in frequency of blood flow between the at least two locations is an indication of the presence of liver fibrosis in the subject.

BRIEF DESCRIPTION OF THE DRAWINGS

The accompanying figures, which are incorporated in and constitute a part of this specification, illustrate several aspects described below.

DETAILED DESCRIPTION

Figure 1:
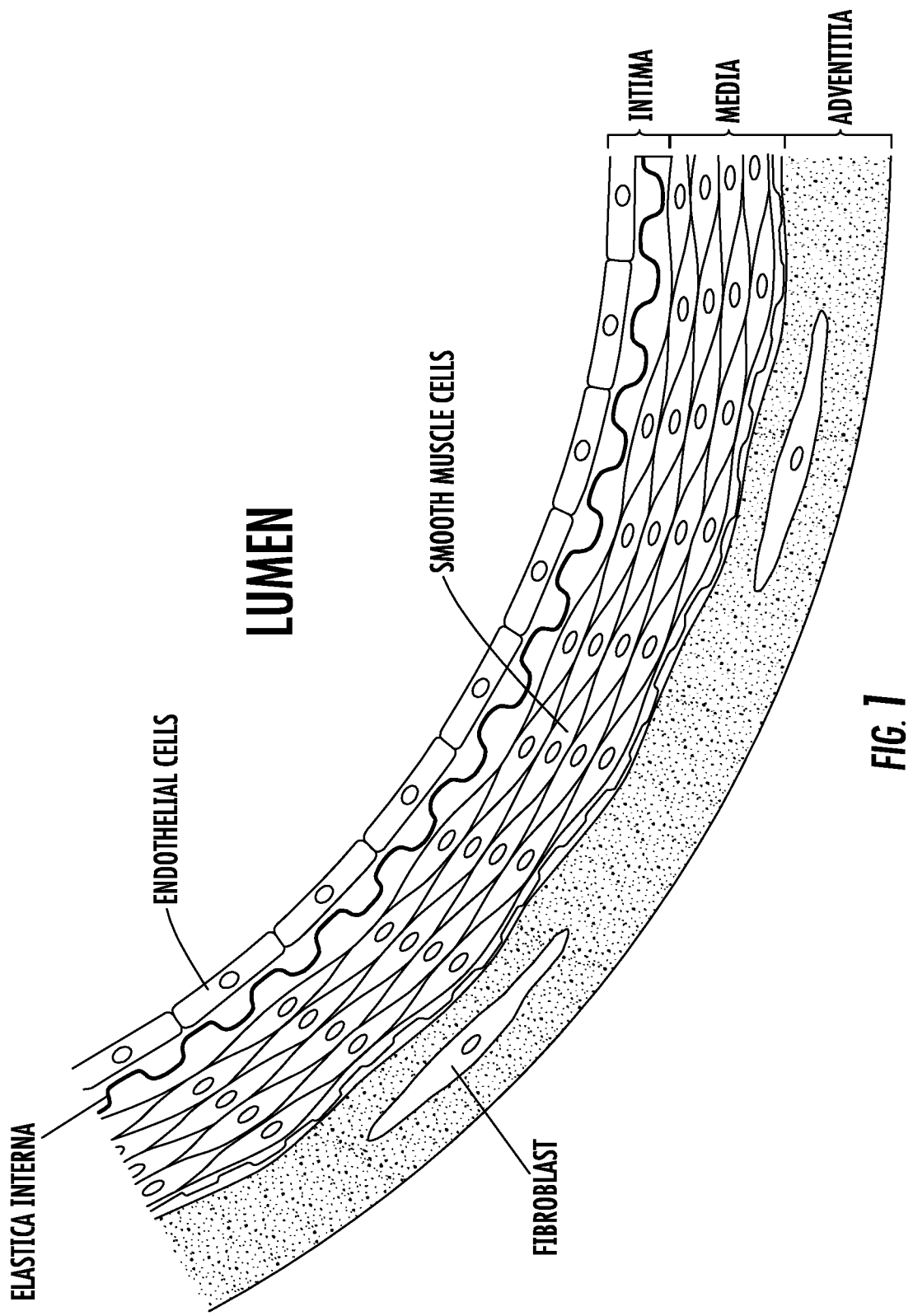
FIG. 1 is a schematic diagram of the layered structure of the wall of a vein.

Disclosed herein are new methods for detecting and diagnosing liver fibrosis. The inventors have developed a noninvasive, accurate liver fibrosis detection method that uses a physics-based machine learning method to analyze data collected using ultrasound devices already available in most hospitals and clinics. These new methods can alleviate the problem of early stage liver fibrosis detection by integrating testing into regular physical exams. In addition, this technology offers a much more convenient and cheaper alternative compared to the current invasive gold-standard liver biopsy.

Reference will now be made in detail to the embodiments of the invention, examples of which are illustrated in the drawings and the examples. This invention may, however, be embodied in many different forms and should not be construed as limited to the embodiments set forth herein.

Unless defined otherwise, all technical and scientific terms used herein have the same meaning as commonly understood to one of ordinary skill in the art to which this invention belongs. The following definitions are provided for the full understanding of terms used in this specification.

Terminology

As used in the specification and claims, the singular form "a," "an," and "the" include plural references unless the context clearly dictates otherwise. For example, the term "a cell" includes a plurality of cells, including mixtures thereof.

As used herein, the terms "may," "optionally," and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

As used here, the terms "stage 0" or "S0" or "grade 0" refers to normal or healthy liver with no detectable fibrosis, very little fibrous tissue in the portal areas and the walls of the central veins, the same as stage 0 of the Metavir fibrosis score.

As used here, the terms "stage 1" or "S1" or "grade 1" refers to liver fibrosis with fibrous expansion of some portal areas, but without short fibrosis septa, the same as stage 1 of the Metavir fibrosis score.

As used here, the terms "stage 2" or "S2" or "grade 2" refers to liver fibrosis with fibrous expansion of most portal areas, with short fibrosis septa, the same as stage 2 of the Metavir fibrosis score.

As used here, the terms "stage 3" or "S3" or "grade 3" refers to liver fibrosis with fibrous expansion of most portal areas, with portal to portal bridging, the same as stage 3 of the Metavir fibrosis score.

As used here, the terms "stage 4" or "S4" or "grade 4" refers to liver fibrosis that has progressed to liver cirrhosis, the same as stage 4 of the Metavir fibrosis score. The term "cirrhosis" is used to describe a chronic liver disease characterized by replacement of liver tissue by fibrous scar tissue as well as regenerative nodules (lumps that occur as a result of a process in which damaged tissue is regenerated), leading to progressive loss of liver function.

As used here, the term "Doppler Ultrasound exam", "Doppler Ultrasound test", "Doppler Ultrasound measurement", or "Doppler Ultrasound image" is used to refer to techniques for estimating the rate of movement of ultrasound scatters. The Doppler principle, in general, describes the perceived or apparent change in frequency, and/or wavelength of a wave by an observer who is moving relative to the wave's source. The apparent change, known as the Doppler effect, may be caused by a motion of the observer, by a motion of the source, or by both a motion of the observer and the source. With respect to ultrasound technology, the term Doppler originated in the continuous wave systems where it applies reliably.

As used herein, the term "frequency of blood flow" generally refers to spatial frequencies of the blood flow, i.e., those components of a traveling waveform that are periodic across position in space as caused by the swelling and contraction of the blood vessels due to the pumping of blood through the body. The "frequency of blood flow" is correlated with the velocity of blood flow and these frequency components can be determined by a Fourier transform of a time-domain representation of the waveform. It should be noted that the Doppler frequency is generally in the hundreds of Hz to kHz range, and the different Doppler Ultrasound usages should be apparent to one skilled in the art.

As used herein, the terms "hepatic" or "liver" are recognized in the art to refers generally to a largest gland in the body, which is situated slightly below the diaphragm and anterior to the stomach. It consists of two lobes which are wedge-shaped.

The term "about" as used herein when referring to a measurable value such as an amount, a percentage, and the like, is meant to encompass variations of ±20%, ±10%, ±5%, or ±1% from the measurable value.

As used here, the terms "beneficial agent" and "active agent" are used interchangeably herein to refer to a chemical compound or composition that has a beneficial biological effect. Beneficial biological effects include both therapeutic effects, i.e., treatment of a disorder or other undesirable physiological condition, and prophylactic effects, prevention of a disorder or other undesirable physiological condition. The terms also encompass pharmaceutically acceptable, pharmacologically active derivatives of beneficial agents specifically mentioned herein, including, but not limited to, salts, esters, amides, prodrugs, active metabolites, isomers, fragments, analogs, and the like. When the terms "beneficial agent" or "active agent" are used, then, or when a particular agent is specifically identified, it is to be understood that the term includes the agent per se as well as pharmaceutically acceptable, pharmacologically active salts, esters, amides, prodrugs, conjugates, active metabolites, isomers, fragments, analogs, etc.

As used herein, the terms "treating" or "treatment" of a subject includes the administration of a drug to a subject with the purpose of preventing, curing, healing, alleviating, relieving, altering, remedying, ameliorating, improving, stabilizing or affecting a disease or disorder, or a symptom of a disease or disorder. The terms "treating" and "treatment" can also refer to reduction in severity and/or frequency of symptoms, elimination of symptoms and/or underlying cause, prevention of the occurrence of symptoms and/or their underlying cause, and improvement or remediation of damage.

As used herein, the term "preventing" a disorder or unwanted physiological event in a subject refers specifically to the prevention of the occurrence of symptoms and/or their underlying cause, wherein the subject may or may not exhibit heightened susceptibility to the disorder or event.

By the term "effective amount" of a therapeutic agent is meant a nontoxic but sufficient amount of a beneficial agent to provide the desired effect. The amount of beneficial agent that is "effective" will vary from subject to subject, depending on the age and general condition of the subject, the particular beneficial agent or agents, and the like. Thus, it is not always possible to specify an exact "effective amount." However, an appropriate "effective" amount in any subject case may be determined by one of ordinary skill in the art using routine experimentation. Also, as used herein, and unless specifically stated otherwise, an "effective amount" of a beneficial can also refer to an amount covering both therapeutically effective amounts and prophylactically effective amounts.

An "effective amount" of a drug necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation.

As used herein, a "therapeutically effective amount" of a therapeutic agent refers to an amount that is effective to achieve a desired therapeutic result, and a "prophylactically effective amount" of a therapeutic agent refers to an amount that is effective to prevent an unwanted physiological condition. Therapeutically effective and prophylactically effective amounts of a given therapeutic agent will typically vary with respect to factors such as the type and severity of the disorder or disease being treated and the age, gender, and weight of the subject.

The term "therapeutically effective amount" can also refer to an amount of a therapeutic agent, or a rate of delivery of a therapeutic agent (e.g., amount over time), effective to facilitate a desired therapeutic effect. The precise desired therapeutic effect will vary according to the condition to be treated, the tolerance of the subject, the drug and/or drug formulation to be administered (e.g., the potency of the therapeutic agent (drug), the concentration of drug in the formulation, and the like), and a variety of other factors that are appreciated by those of ordinary skill in the art.

As used herein, the term "subject" or "host" can refer to living organisms such as mammals, including, but not limited to humans, livestock, dogs, cats, and other mammals. Administration of the therapeutic agents can be carried out at dosages and for periods of time effective for treatment of a subject. In some embodiments, the subject is a human. In some embodiments, the pharmacokinetic profiles of the systems of the present invention are similar for male and female subjects.

Liver Fibrosis

Liver fibrosis, which is caused by chronic liver diseases, can affect the function of liver, and is a major public health problem around world. Liver fibrosis has a strong correlation with other diseases, including diabetes and cancer. Recently, the understanding of physiology and pathophysiology in liver fibrosis has improved the quality of life for many patients.

Pathohistologically, liver fibrosis appears as the replacement of injured liver tissue by collagen fibers. Its progression depends on the many factors from liver disease and environment. As liver fibrosis progresses, collagen fiber accumulation in the lobule prevents the exchange nutrient between the blood and the normal tissue. The progression of liver fibrosis is divided into five stages (S0 to S4) of the Metavir fibrosis score.

S0: Little fibrous tissue in the portal areas and central veins.

S1: Fibrous expansion of some portal areas, without short fibrosis septa.

S2: Fibrous expansion of most portal areas, with short fibrosis septa.

S3: Fibrous expansion of most portal areas, with portal to portal bridging.

S4: Cirrhosis.

At each stage of liver fibrosis, the fibrous growth accompanies the distortion of the hepatic vasculature. This leads to an alteration of blood flow in the portal vein and sinusoid, and decreases the exchange of substances between hepatic vessel and the adjacent liver parenchyma.

Currently, there are several techniques being explored to diagnose liver fibrosis. These include both invasive and noninvasive measurement. Liver biopsy is an invasive diagnosis and is still considered the gold standard for hepatic fibrosis. However, the accuracy of liver biopsy is only 65%-75% when the biopsies are between 15 mm and 25 mm in length. The invasive procedure also includes a high risk of operation in some pathophysiologies, such as liver cancer, and can cause significant pain for patients.

The current noninvasive procedures use ultrasound testing of the stiffness of liver and offer low accuracy. The low accuracy can be due to either instrument accuracy or the subjectivity of operators, or both. Because the liver is a large organ and deeply embedded in the body, other tissues and organs may affect the activity of ultrasound and make the liver fibrosis grading difficult.

Many studies have demonstrated the significant positive correlation between the stiffness of liver and the stage of liver fibrosis. The mechanical properties of liver are modified by the growth collagen fiber network and can be described by the physical parameters of the liver.

A physics-based mathematical model was developed by the inventors, which constructs a new relationship between the dynamic of blood flow and the mechanical properties of the liver tissue. The mathematical model predicts the relationship between the stages of liver fibrosis and a key feature of the blood flow, and the results have been validated by Doppler Ultrasound images from hepatic fibrosis patients.

While Doppler Ultrasound has been used to measure blood flow velocity for many years, it has not been used to detect and diagnose liver fibrosis. The well-known Doppler shift phenomenon provides that ultrasonic signals reflected from moving targets will have a shift in frequency directly proportional to the target velocity parallel to the direction of the ultrasound beam. The frequency shift is the same for any object moving at a given velocity, whereas the amplitude of the detected signal is a function of the acoustic reflectivity of the moving object reflecting the ultrasound. Pulse Doppler Ultrasound systems commonly produce a spectrogram of the detected return signal frequency (i.e., velocity) as a function of time in a particular sample volume, with the spectrogram being used by a physician to determine blood flow characteristics of a patient. Standard guidelines for Doppler Ultrasound imaging are applied and are known in the art.

The results and methods disclosed herein provide a new noninvasive diagnostic tool for liver fibrosis.

Methods for Detecting Fibrosis

The invention herein is directed to new and useful methods for the noninvasive detection of liver fibrosis. While these methods involve the known Doppler Ultrasound technique, these methods apply this technology in a non-conventional manner, such that the inventors were the first to establish the relationship between Doppler Ultrasound frequency shift differences in the hepatic and portal veins and the presence of liver fibrosis.

The previous gold standard for detecting liver fibrosis included liver biopsy. The invasive method was painful, expensive, and time-consuming. Thus, the inventors used instrumentation that would not conventionally be used by doctors wanting to detect liver fibrosis. The use of Doppler Ultrasound in such an unconventional manner allows doctors to reduce errors, while providing a noninvasive technology to the patient.

As no one in the field was comparing wave frequencies to diagnose liver fibrosis, the elements of the invention were not well-known and conventional to those skilled in the art. For example, a recent scientific journal article (Doppler ultrasonography combined with transient elastography improves the noninvasive assessment of fibrosis in patients with chronic liver diseases. Alempijevic T et. al Med Ultrason. 2017 Jan. 31; 19(1):7-15) reflects the techniques used in state-of-the-art ultrasound studies to diagnose liver fibrosis. These involve the following parameters: hepatic artery diameter, hepatic artery systolic and diastolic velocity, splenic artery systolic velocity and splenic artery resistance index. Conspicuously absent is any reference to the inventor's improved methods, which ascertain the relative flow dynamics (via wave frequencies) in the portal and hepatic veins as indicia of liver fibrosis. The methods herein allow for a more refined discernment of early stage fibrosis.

Additionally, prior to the methods of the present invention, previous attempts at noninvasive methods to detect liver fibrosis suffered from a number of shortcomings, including but not limited to, inter-operator variability, heterogeneity, non-discrimination between fatty liver and fibrotic liver, echogenicity was poorly predictive, and efficacy limited in obese patients. In contrast, the present invention improved inter-operator variability by calculating frequency level, which is not subjected to the inter-operator variability and is determined by the condition of the tissue rigidity. In addition, the methods herein do not rely on density images. Finally, the methods disclosed herein are unaffected by the thickness of fat layers and thus do not have limited efficacy in obese patient populations.

Disclosed herein are new methods for detecting and diagnosing liver fibrosis using Doppler ultrasound.

In one aspect, provided herein is a method for detecting liver fibrosis in a subject, comprising the steps:
measuring the subject's heart beat rate;
measuring frequency of blood flow by Doppler Ultrasound in a portal vein of the subject;
measuring frequency of blood flow by Doppler Ultrasound in one of the hepatic veins of the subject; and
determining the presence of a shift in the frequency of blood flow in the hepatic vein as compared to the frequency of blood flow in the portal vein; wherein an increase in the frequency of blood flow in the hepatic vein as compared to the frequency of blood flow in the portal vein is an indication of liver fibrosis.

In some embodiments, the frequency of blood flow is measured by Doppler Ultrasound in at least two locations in the hepatic veins of the subject, in some embodiments, the frequency of blood flow is measured by Doppler Ultrasound in three locations in the hepatic veins of the subject.

In some embodiments, the presence of a shift in the frequency of blood flow in the hepatic vein as compared to the frequency of blood flow in the portal vein of between about 0.0068 Hz and about 0.0200 Hz is an indication of stage 1 liver fibrosis. In some embodiments, the presence of a shift in the frequency of blood flow in the hepatic vein as compared to the frequency of blood flow in the portal vein of between 0.0068 Hz and 0.0200 Hz is an indication of stage 1 liver fibrosis.

In some embodiments, the presence of a shift in the frequency of blood flow in the hepatic vein as compared to the frequency of blood flow in the portal vein of between about 0.0200 Hz to about 0.0251 Hz is an indication of stage 2 liver fibrosis. In some embodiments, the presence of a shift in the frequency of blood flow in the hepatic vein as compared to the frequency of blood flow in the portal vein of between 0.0200 Hz to 0.0251 Hz is an indication of stage 2 liver fibrosis.

In some embodiments, the presence of a shift in the frequency of blood flow in the hepatic vein as compared to the frequency of blood flow in the portal vein of between about 0.0251 Hz to about 0.0401 Hz is an indication of stage 3 liver fibrosis. In some embodiments, the presence of a shift in the frequency of blood flow in the hepatic vein as compared to the frequency of blood flow in the portal vein of between 0.0251 Hz to 0.0401 Hz is an indication of stage 3 liver fibrosis.

In some embodiments, the presence of a shift in the frequency of blood flow in the hepatic vein as compared to the frequency of blood flow in the portal vein of greater than about 0.0401 Hz is an indication of stage 4 liver fibrosis (stage 4 liver fibrosis is also referred to as cirrhosis). In some embodiments, the presence of a shift in the frequency of blood flow in the hepatic vein as compared to the frequency of blood flow in the portal vein of greater than 0.0401 Hz is an indication of stage 4 liver fibrosis.

In some embodiments, the presence of a shift in the frequency of blood flow in the hepatic vein as compared to the frequency of blood flow in the portal vein of greater than about 0.045 is an indication of stage 4 liver fibrosis. In some embodiments, the presence of a shift in the frequency of blood flow in the hepatic vein as compared to the frequency of blood flow in the portal vein of greater than 0.045 is an indication of stage 4 liver fibrosis.

In some embodiments, the presence of a shift in the frequency of blood flow in the hepatic vein as compared to the frequency of blood flow in the portal vein of greater than about 0.05 is an indication of stage 4 liver fibrosis. In some embodiments, the presence of a shift in the frequency of blood flow in the hepatic vein as compared to the frequency of blood flow in the portal vein of greater than 0.05 is an indication of stage 4 liver fibrosis.

In some embodiments, the presence of a shift in the frequency of blood flow in the hepatic vein as compared to the frequency of blood flow in the portal vein of greater than about 0.055 is an indication of stage 4 liver fibrosis. In some embodiments, the presence of a shift in the frequency of blood flow in the hepatic vein as compared to the frequency of blood flow in the portal vein of greater than 0.055 is an indication of stage 4 liver fibrosis.

In some embodiments, the presence of a shift in the frequency of blood flow in the hepatic vein as compared to the frequency of blood flow in the portal vein of greater than about 0.06 is an indication of stage 4 liver fibrosis. In some embodiments, the presence of a shift in the frequency of blood flow in the hepatic vein as compared to the frequency of blood flow in the portal vein of greater than 0.06 is an indication of stage 4 liver fibrosis.

In some embodiments, the subject is treated with a therapeutic agent if the frequency of blood flow in the hepatic vein is increased as compared to the frequency of blood flow in the portal vein. In some embodiments; the therapeutic agent is selected from an antiviral agent; antibiotic, a diuretic, or a laxative.

In another aspect, disclosed herein is a method for detecting liver fibrosis in a subject, comprising the steps:
  measuring the subject's heart beat rate;
  measuring the frequency of blood flow in at least two locations in a subject's liver using a Doppler Ultrasound system;
  determining a shift in frequency of blood flow between the at least two locations in the liver;
  wherein the shift in frequency of blood flow between the at least two locations is an indication of the presence of liver fibrosis in the subject.

In addition to the liver, dynamic blood low measurements (detecting frequency shifts of blood flow) are also used for detecting disease in other organs of the body. For example, the methods described herein can be used in the lungs (for detection and diagnosis of cystic fibrosis, idiopathic pulmonary fibrosis, or radiation-induced lung injury following treatment for cancer), heart (for detection and diagnosis of atrial fibrosis, endomyocardial fibrosis, and old myocardial infarction), brain (for detection and diagnosis of glial scarring), kidney, and/or spleen. In addition, dynamic blood measurements of other organs can also be used for detecting diseases such as arterial stiffness; arthrofibrosis (knee, shoulder; other joints); Crohn's Disease (intestine); dupuytren's contracture (hands, fingers); keloid (skin); mediastinal fibrosis (soft tissue of the mediastinum); myelofibrosis (bone marrow); peyronie's disease (penis); nephrogenic systemic fibrosis (skin); progressive massive fibrosis (lungs; a complication of coal workers' pneumoconiosis); retroperitoneal fibrosis (soft tissue of the retroperitoneum); scleroderma/systemic sclerosis (skin, lungs); and some forms of adhesive capsulitis (shoulder).

In another aspect, disclosed herein is a method for detecting fibrosis (fibrotic disease) in an organ of a subject, comprising the steps:
  measuring the subject's heart beat rate;
  measuring the frequency of blood flow in at least two locations in the organ of the subject using a Doppler Ultrasound system;
  determining a shift in frequency of blood flow between the at least two locations in the organ of the subject;
  wherein the shift in frequency of blood flow between the at least two locations is an indication of the presence of fibrosis (fibrotic disease) in the subject.

In one aspect, provided herein is a method for detecting a shift in the frequency of blood flow in the hepatic vein as compared to the frequency of blood flow in the portal vein in a subject, comprising the steps:
  measuring the subject's heart beat rate;
  measuring frequency of blood flow by Doppler Ultrasound in the portal vein of the subject;
  measuring frequency of blood flow by Doppler Ultrasound in the hepatic vein of the subject; and
  determining the presence of a shift in the frequency of blood flow in the hepatic vein as compared to the frequency of blood flow in the portal vein.

Also disclosed herein is a method for the detection of liver fibrosis in a subject, comprising: measuring frequency of blood flow in the portal vein of the subject and measuring frequency of blood flow in the hepatic vein of the subject by a Doppler Ultrasound device moving over a region of skin to electronically determine a shift in the frequency of blood flow in the hepatic vein as compared to the frequency of blood flow in the portal vein.

Further disclosed herein is a method for the detection of liver fibrosis in a subject, comprising:
- monitoring variations in frequency of blood flow by Doppler Ultrasound in the portal vein of the subject and frequency of blood flow by Doppler Ultrasound in the hepatic vein of the subject;
- analyzing the monitored variations to determine the presence of a shift in the frequency of blood flow in the hepatic vein as compared to the frequency of blood flow in the portal vein; and
- determining the presence of a shift in the frequency of blood flow in the hepatic vein as compared to the frequency of blood flow in the portal vein; wherein an increase in the frequency of blood flow in the hepatic vein as compared to the frequency of blood flow in the portal vein is an indication of liver fibrosis.

Therapeutics for Treating Liver Fibrosis

In additional aspects, disclosed herein are additional steps to the methods where a subject is further treated with a therapeutic agent. In some embodiments, the subject is treated with a therapeutic agent (or therapeutic treatment) if the frequency of blood flow in the hepatic vein is increased as compared to the frequency of blood flow in the portal vein. In some embodiments, the therapeutic agent is selected from an antiviral agent, antibiotic, a diuretic, or a laxative.

In one aspect, provided herein is a method for treating or preventing liver fibrosis in a subject, comprising the steps:
- measuring the subject's heart beat rate;
- measuring frequency of blood flow by Doppler Ultrasound in a portal vein of the subject;
- measuring frequency of blood flow by Doppler Ultrasound in a hepatic vein of the subject;
- determining the presence of a shift in the frequency of blood flow in the hepatic vein as compared to the frequency of blood flow in the portal vein; wherein an increase in the frequency of blood flow in the hepatic vein as compared to the frequency of blood flow in the portal vein is an indication of liver fibrosis; and
- administering a therapeutic agent, or therapeutic treatment, if the frequency of blood flow in the hepatic vein is increased as compared to the frequency of blood flow in the portal vein.

In some embodiments, the therapeutic agent is administered for the treatment of liver fibrosis, or in some embodiments, the therapeutic agent is administered for the prevention of the progression of liver fibrosis (for example, progression between stages of liver fibrosis). In some embodiments, the therapeutic agent is administered in an effective amount sufficient to treat the associated symptoms of liver fibrosis.

In some embodiments, the subject is treated with a therapeutic agent if the frequency of blood flow in the hepatic vein is increased as compared to the frequency of blood flow in the portal vein.

In some embodiments, the therapeutic agent is selected from an antiviral agent, antibiotic, a diuretic, or a laxative. Other therapeutic agents that can be administered to subjects can include thiamine, steroids, acetylcysteine, or pentoxifylline.

Antibiotics can be prescribed to help clear infections. Patients with decompensated cirrhosis generally require admission to a hospital and monitoring of fluid balance, for example, with diuretics. Diuretics may be necessary to suppress ascites. Diuretic options for inpatient treatment include aldosterone antagonists (spironolactone) and loop diuretics. Laxatives, such as lactulose, can be prescribed for decreasing the risk of associated constipation.

However, generally liver damage from cirrhosis cannot be reversed, and liver transplantation is necessary for many late stage patients. Therefore, the methods disclosed can improve early stage detection, and help decrease the need for expensive and complicated liver transplantations. In some embodiments, the therapeutic treatment is a liver transplant.

Cirrhosis can also commonly be caused by hepatitis B or hepatitis C. In some embodiments, the subject is further treated with an antiviral agent. In some embodiments, the antiviral agent is selected from sofosbuvir, simeprevir, ledipasvir, paritaprevir, ombitasvir, dasabuvir, peginterferon and ribavirin, or a combination thereof.

In one embodiment, the level of liver fibrosis, which is the formation of fibrous tissue, fibroid or fibrous degeneration, is reduced by more than about 90% by the therapeutic agent. In one embodiment, the level of fibrosis, which is the formation of fibrous tissue, fibroid or fibrous degeneration, is reduced by at least about 90%, at least about 80%, at least about 70%, at least about 60%, at least about 50%, at least about 40%, at least about 30%, at least about 20%, at least about 10%, at least about 5% or at least about 2%.

The methods herein represent a completely new approach for assessing liver fibrosis to provide for earlier intervention and prevention and/or treatment of liver fibrosis. The marked improvement of Doppler technologies and the unconventional application of the Doppler Ultrasound to perform measurement at multiple locations, allowed the inventors for the first time to detect liver fibrosis in a subject, comprising the steps: measuring the subject's heart beat rate: measuring frequency of blood flow by Doppler Ultrasound in a portal vein of the subject; measuring frequency of blood flow by Doppler Ultrasound in a hepatic vein of the subject; and determining the presence of a shift in the frequency of blood flow in the hepatic vein as compared to the frequency of blood flow in the portal vein; wherein an increase in the frequency of blood flow in the hepatic vein as compared to the frequency of blood flow in the portal vein is an indication of liver fibrosis.

EXAMPLES

The following example is set forth below to illustrate the theory, devices, methods, and results according to the disclosed subject matter. This example is not intended to be inclusive of all aspects of the subject matter disclosed herein, but rather to illustrate representative methods and results. This example is not intended to exclude equivalents and variations of the present invention which are apparent to one skilled in the art.

Example 1. Dynamics of Blood Flow in Liver to Discriminate Hepatic Fibrosis Grades Cirrhosis is a significant public health problem. Early stages of liver fibrosis are asymptomatic and difficult to diagnose. In collaboration with clinicians specialized in hepatic fibrosis, the inventors have developed a physics-based mathematical model to integrate an empirical understanding of fibrosis development, which connects the fibrosis stage to the mechanical properties (stiffness) of the tissue and organ and the blood flow dynamics. The model predicts the consequential blood flow pattern changes as the tissue stiffness surround the portal vein changes. The prediction has been supported by Doppler Ultrasound measurements from hepatic fibrosis patients. The specific correspondence of flow dynamics to fibrosis stage is determined through machine learning using the same hepatic fibrosis patient data. Therefore, this model and analysis of Doppler Ultrasound images provides a new noninvasive diagnostic tool for all stages of liver fibrosis.

As liver fibrosis progresses, the deposition of collagen increases the stiffness of the liver tissue, which effects the blood flow in the portal and hepatic veins. The wall of the veins consists of three layers: intima, media and adventitia (FIG. 1). The intima layer is comprised of endothelial cells and a basement membrane; this smooth interface between the tissue and the blood is also a protective barrier. The media layer is comprised of smooth muscle cells that provide elasticity for the vascular wall. Smooth muscle expansion and contraction in the media layer provides the main driving force for blood flow in vein. The adventitia layer includes fibroblast cells, which produce and deposit collagen fibers when activated.

Figure 2:
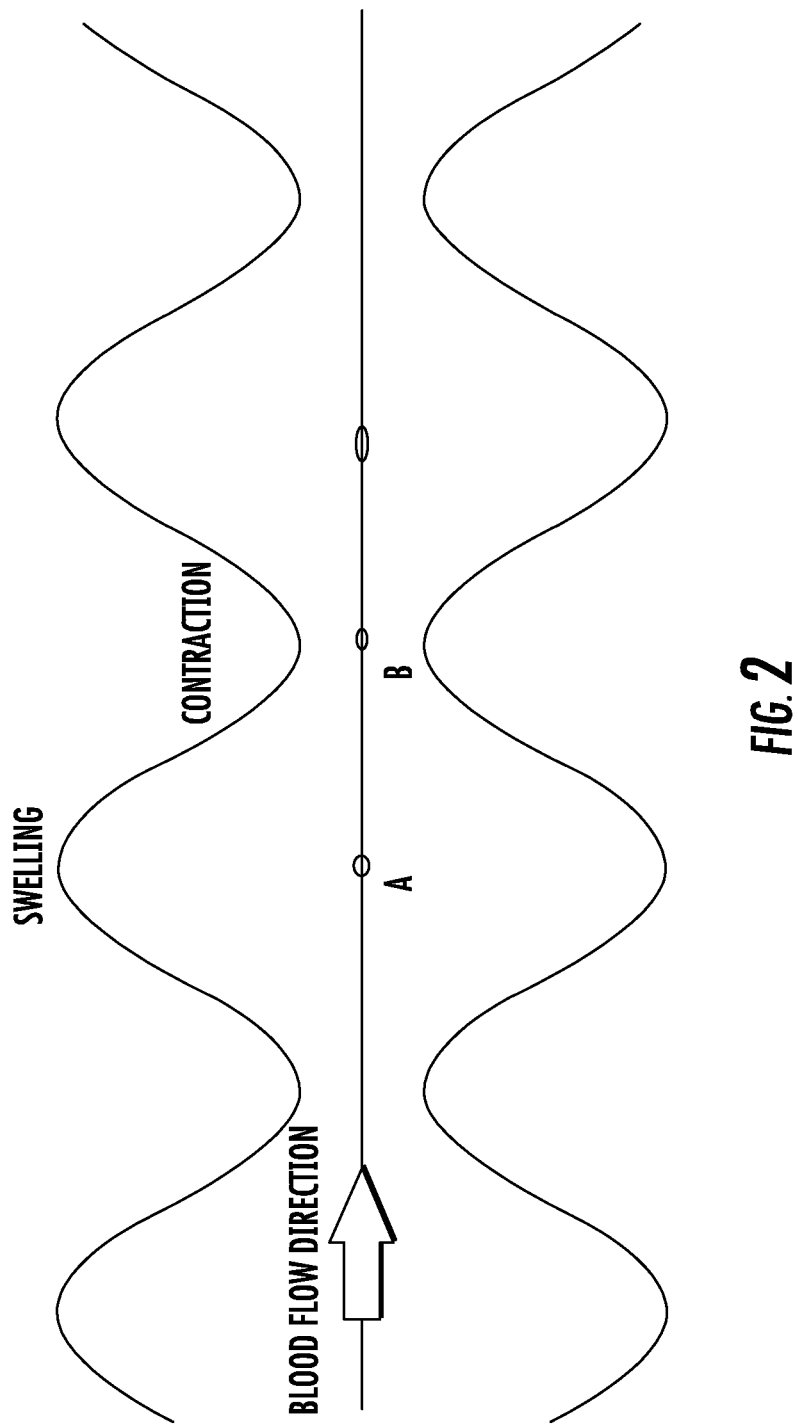
FIG. 2 is a schematic diagram of the wave pattern of blood flow caused by the swelling and contraction of the vein.

During the progression of hepatic fibrosis, in the adventitia layer, activated fibroblasts (called myofibroblasts) release collagen fibers in the adventitia. The collagen fibers cross-link to form a fiber network that gradually encloses the vein, and restricts the smooth muscle's ability to expand, hence modifying the blood flow pattern in the vein. This modification can be quantified when the smooth muscle is considered as an elastic material. When a pulse of blood flows the through the vein, smooth muscle layer expands to accommodate the extra volume, effectively converting the kinetic energy of the blood flow into the elastic potential energy. Once its potential energy reaches a threshold, the muscle layer begins to contract, which converts the potential energy to the kinetic energy of blood. Thus, the lowest velocity of blood occurs at point A and the highest velocity of blood at point B (FIG. 2). Similar oscillation is repeated at each point along the vessel wall of the vein, the driving force of which is the pressure force from the pulsing blood flow.

Under normal conditions, the smooth muscle contraction has the same frequency as the pressure force. The oscillation can be approximated as a harmonic oscillation, where the motion of each point is described as $$m\ddot{x}+kx=0,$$

in which m is mass of each point, k is elastic rigidity of the smooth muscle layer, and x is the displacement of each point. Solving the equation of motion yields:

$$x(t)=A\cos(\omega t+\varphi),$$

where A is the amplitude of the oscillation and the angular velocity $\omega$ is related to the oscillation frequency f.

$$\omega = \sqrt{\frac{k}{m}} = 2\pi f.$$

In the case of hepatic fibrosis, the fiber network encapsulates the vein, effectively increasing the elastic rigidity of the vessel wall: $k_{fibrosis}>k$. Energy conservation requires that the product of the rigidity and the amplitude squared remains constant. Hence the amplitude of oscillation is decreased as $$A_{fibrosis} = \sqrt{\frac{k}{k_{fibrosis}}} A_2$$

Next, the motion is of the vessel wall is still described as $$x(t) = A_{fibrosis}(\omega t + \varphi) \text{ where}$$

$$\omega = \sqrt{\frac{k_{fibrosis}}{m}} = 2\pi f_{fibrosis} > 2\pi f$$

This shows that the frequency of vessel wall oscillation in a fibrotic liver should be greater than in a normal liver. Because the flow velocity of blood is caused by the oscillation of vein, the frequency of the blood flow velocity also should show the same trend.

Figure 3:
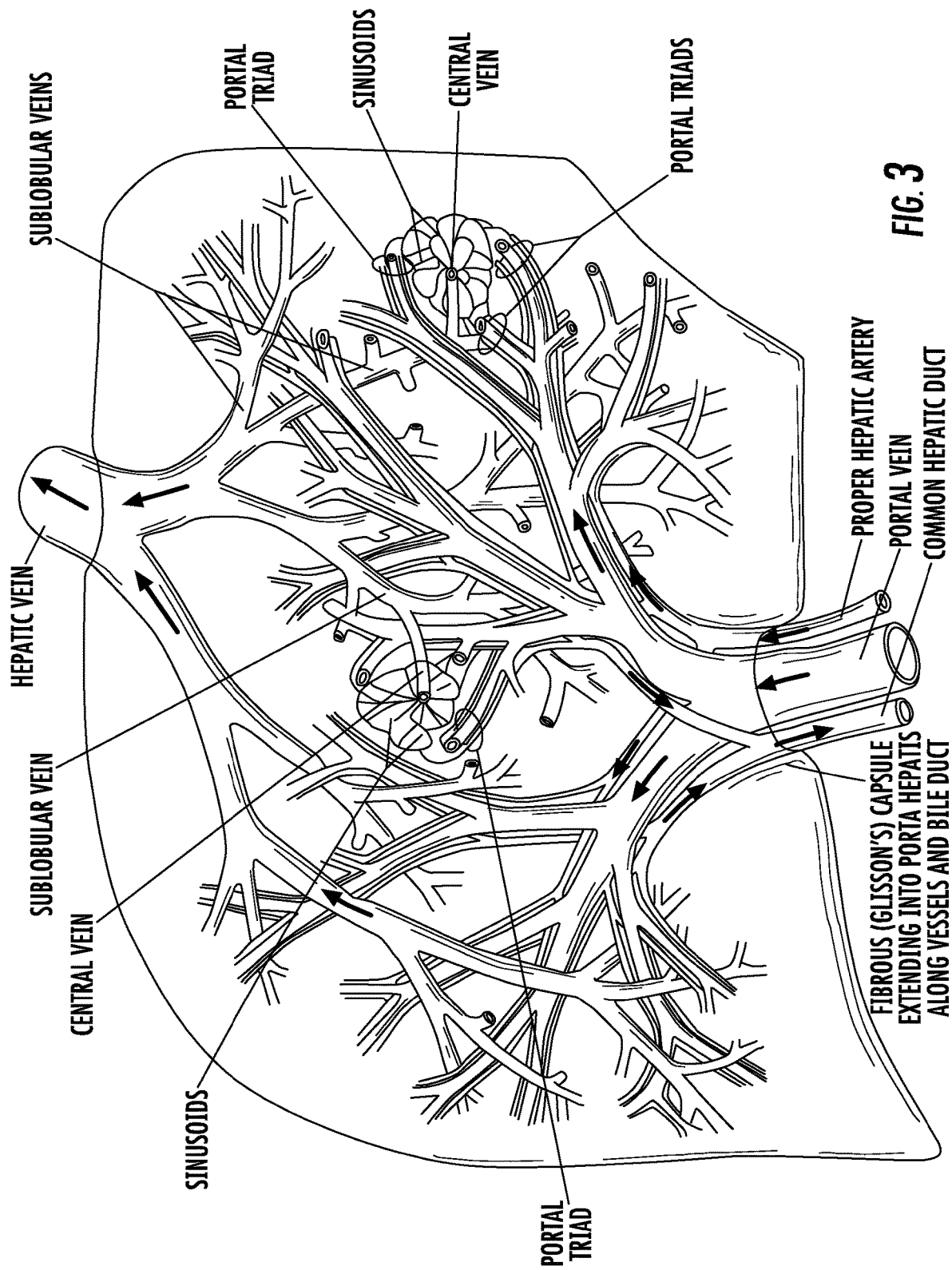
FIG. 3 is a schematic diagram of the vein structure and organization in the liver.

In the liver, blood enters the organ through the portal vein, diffuses through the liver tissue, then exits from the hepatic vein (FIG. 3). As fibrosis increases the rigidity of the liver tissue, it is to be expected that the difference between the entrance and exit blood flow would reflect the rigidity change of the liver. In order to show that the frequency of the blood flow velocity is correlated with and responds to the stiffness of vascular wall, the velocity of blood was measured by Doppler Ultrasound from the portal vein and the hepatic vein, respectively.

Figure 4A:
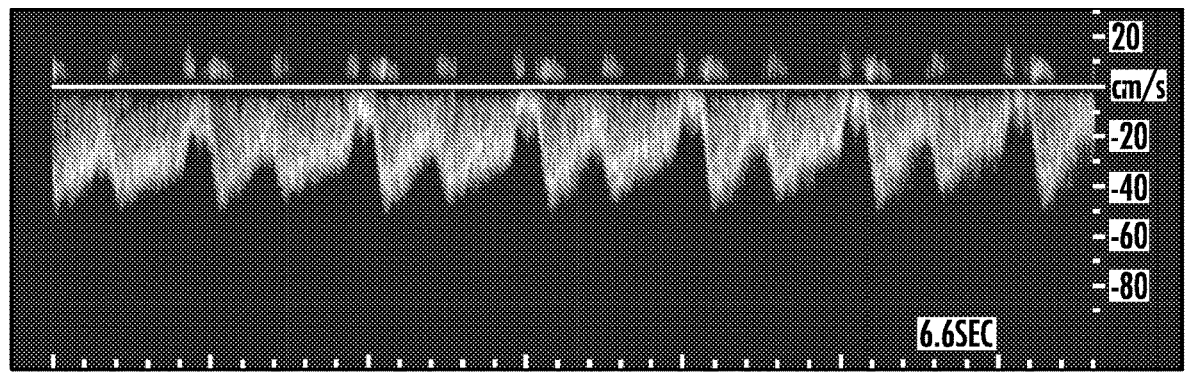
FIG. 4A is a Doppler Ultrasound image of the middle hepatic vein of a patient. The horizontal axis is time. The example shown here was recorded a total of 6.6 seconds. The vertical axis is blood flow speed where the unit is cm/s.
Figure 4B:
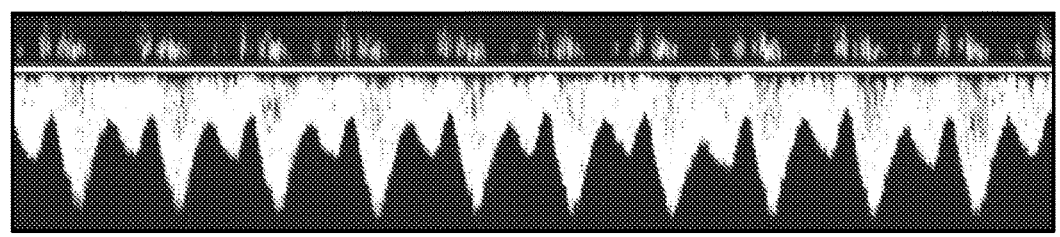
FIG. 4B is a pre-processed Doppler Ultrasound image with the axis information removed.
Figure 4C:
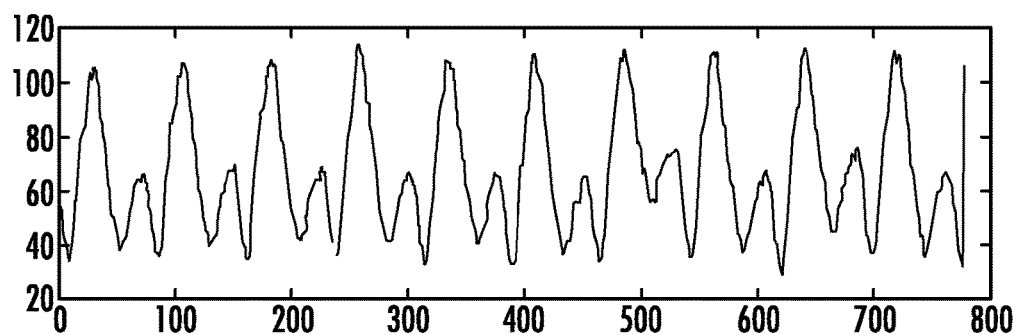
FIG. 4C is the processed image of FIG. 4B showing the boundary of the wave pattern of the blood flow.

Doppler Ultrasound imaging uses high-frequency sound waves to measure the blood flow velocity in the liver over a period of observation (FIG. 4A). The wave pattern of the blood flow velocity was extracted from the ultrasound image (FIG. 4B). The envelop of the wave pattern (FIG. 4C) was extracted and further analyzed.

Figure 5:
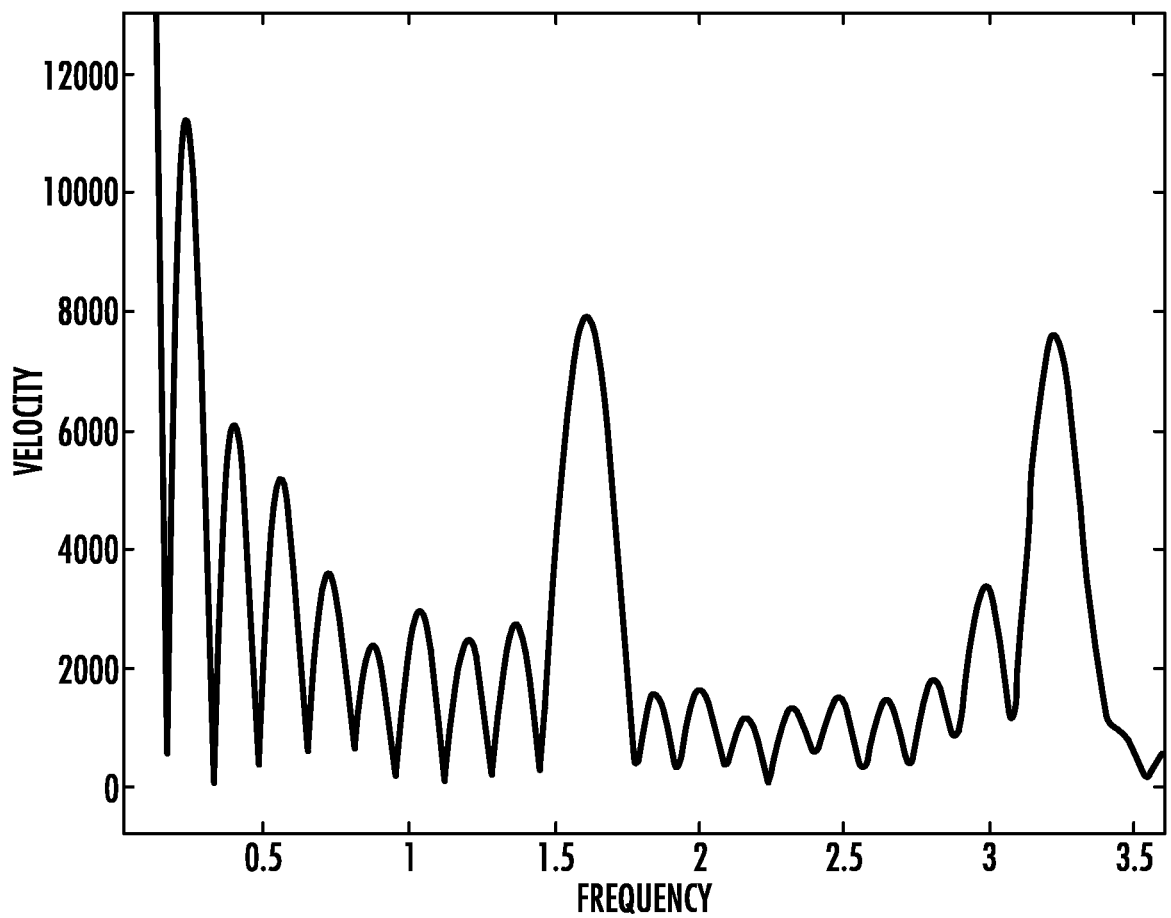
FIG. 5 shows the Fourier transformation of the wave pattern in FIG. 4C as velocity vs. frequency. The unit for velocity is cm/s, and the unit for frequency is Hz.

Since the frequency is the main parameter of interest, the curve is transferred from time domain to frequency domain through the Fourier transform, which is written as, $$\hat{f}(\xi)=\int_{-\infty}^{\infty}f(t)e^{-2\pi i t\xi}dt,$$

for any real number $\xi$, and where t represents time (FIG. 5). It is discovered through this analysis that the portal vein frequency matches the heart beat frequency perfectly in all the patients with early stage fibrosis (stages 1-3). Hence the heart beat frequency can be used as a reference to select for the signature frequency in portal vein and hepatic vein, respectively.

Figure 6:
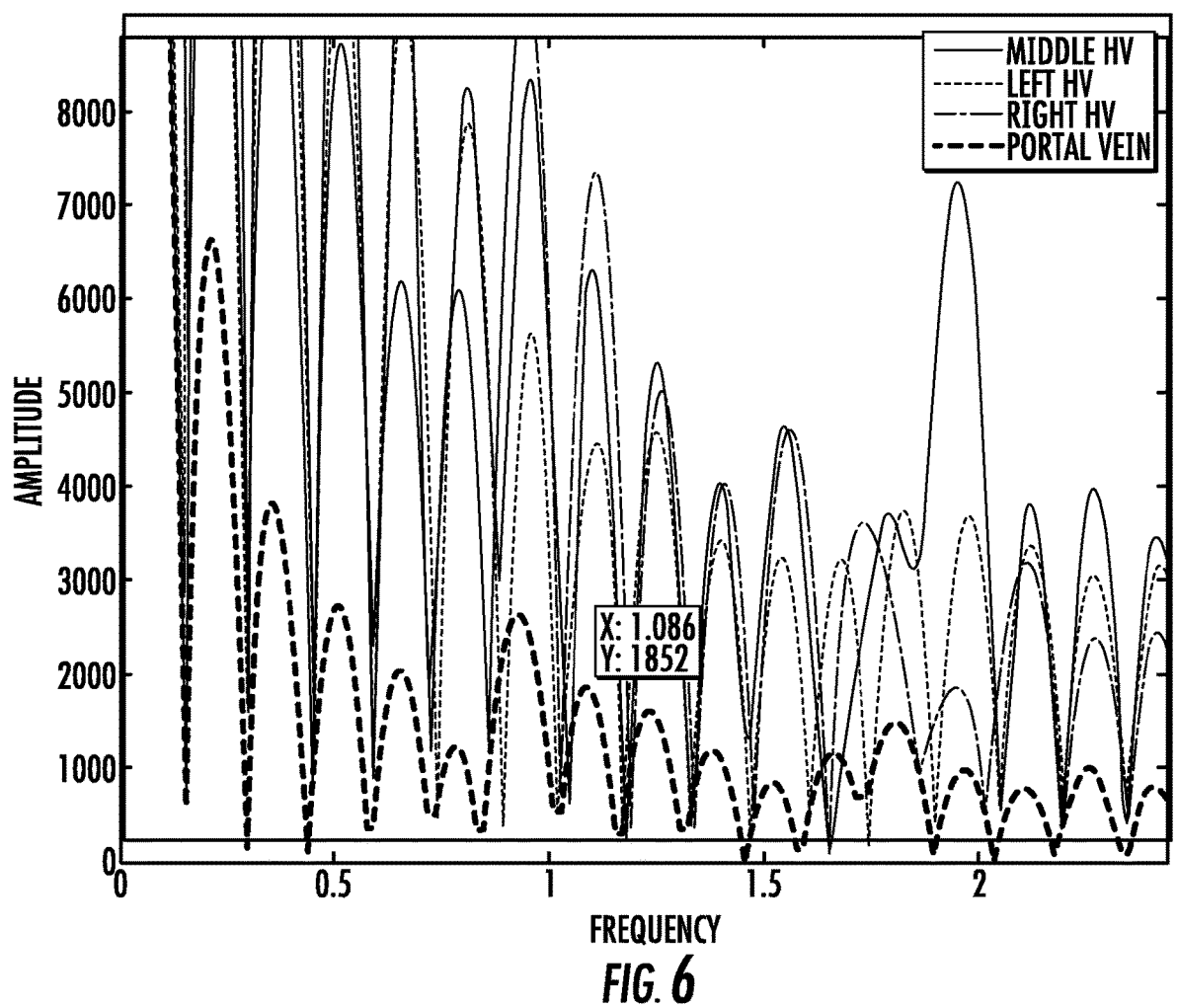
FIG. 6 shows a graph comparing each frequency pattern from a different vein in the liver (portal vein, left hepatic vein, middle hepatic vein, and right hepatic vein). The unit for frequency is Hz, and the unit for blood flow velocity is cm/s.

FIG. 6 shows representative data from one patient. In this example, four Doppler Ultrasound measurements were taken (at the entrance of portal vein, and the exit of the left, middle and right hepatic veins, respectively). The heart beat frequency has been marked in FIG. 6.

To understand the modes of dynamics on how blood flow changes because of excess collagen fibers, the stage of liver fibrosis as measured and determined by the blood flow was considered. Here, the fiber structure leads to restricted deformation of vascular walls. To determine if the fiber-blood model exhibits this global behavior, a simulated blood measurement was utilized. The observed change in the different stages of liver fibrosis were observed in simulations. After an initial increase in tissue pliability, as fiber begins to appear around the vein, the frequency of the peak blood flow velocity shifts to higher values.

Figure 7:
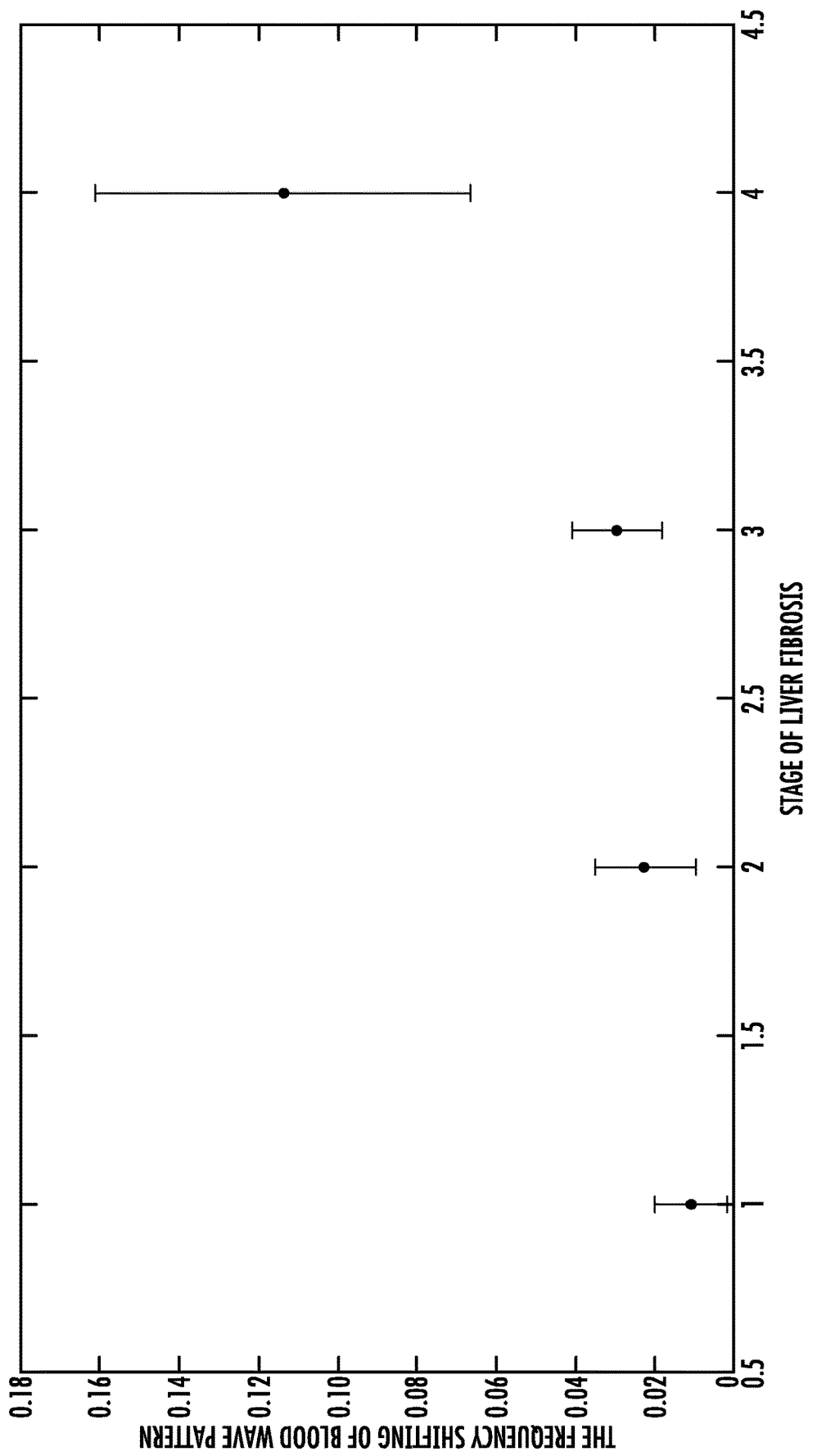
FIG. 7 shows a graph of the frequency shifting of the blood wave pattern the stage of liver fibrosis (stages 1 to 4).

Clinical data were then measured from 200 patients, and 10 healthy controls. Each patient's data includes four ultrasound images (at the entrance of portal vein, and the exit of the left, middle and right hepatic veins, respectively) and a heart rate value. In all healthy controls, the difference between the signature frequencies between the hepatic vein and the portal vein is about 0, or much less than 0.006 Hz. The difference between the signature frequencies between the hepatic vein and the portal vein, or the frequency shift, from 200 patients are plotted as a function of their fibrosis stage as determined by the pathologists (FIG. 7). This plot strongly indicates a positive correlation between the frequency shift and the fibrosis stage. Therefore, analysis of this extensive set of clinical data confirms the results of our model, where the frequencies of blood flow is strongly correlated with the stages of fibrosis. The higher the stage of hepatic fibrosis, the higher the frequency shifting of the wave pattern in the Doppler image (FIG. 7).

In summary, this example describes a new method for diagnosing liver fibrosis. This method models the dynamics of blood flow that change as a result of liver fibrosis. The method further shows how Doppler Ultrasound measurements can be used to diagnose the stage of liver fibrosis in a patient. These observations avoid confusion from the effects from other diseases and the physiological state of the patient's body because the focus is on the physical correlation between the collagen fiber structure in fibrotic liver and the blood flow. The results from the data collected from these patients show that this noninvasive method has provided a new paradigm for liver fibrosis diagnosis and has facilitated a better understanding of liver fibrosis.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

We claim:

1. A method for detecting liver fibrosis in a subject, comprising the steps:
    measuring the subject's heartbeat rate;
    measuring frequency of blood flow by Doppler Ultrasound in a portal vein of the subject;
    measuring frequency of blood flow by Doppler Ultrasound in a hepatic vein of the subject; and
    determining the presence of a shift in the frequency of blood flow in the hepatic vein as compared to the frequency of blood flow in the portal vein; wherein an increase in the frequency of blood flow in the hepatic vein as compared to the frequency of blood flow in the portal vein is an indication of liver fibrosis.

2. The method of claim 1, wherein the frequency of blood flow is measured by Doppler Ultrasound in at least two locations in the hepatic vein of the subject.

3. The method of claim 1, wherein the frequency of blood flow is measured by Doppler Ultrasound in three locations in the hepatic vein of the subject.

4. The method of claim 1, wherein the presence of a shift in the frequency of blood flow in the hepatic vein as compared to the frequency of blood flow in the portal vein of greater than about 0.0401 Hz is an indication of stage 4 liver fibrosis.

5. The method of claim 1, wherein the presence of a shift in the frequency of blood flow in the hepatic vein as compared to the frequency of blood flow in the portal vein of greater than about 0.0251 Hz and less than about 0.0401 Hz is an indication of stage 3 liver fibrosis.

6. The method of claim 1, wherein the presence of a shift in the frequency of blood flow in the hepatic vein as compared to the frequency of blood flow in the portal vein of greater than about 0.0200 Hz and less than about 0.0251 Hz is an indication of stage 2 liver fibrosis.

7. The method of claim 1, wherein the presence of a shift in the frequency of blood flow in the hepatic vein as compared to the frequency of blood flow in the portal vein of greater than about 0.0068 Hz and less than about 0.0200 Hz is an indication of stage 1 liver fibrosis.

8. The method of claim 1, wherein the subject is treated with a therapeutic agent if the frequency of blood flow in the hepatic vein is increased as compared to the frequency of blood flow in the portal vein.

9. The method of claim 8, wherein the therapeutic agent is selected from an antiviral agent, antibiotic, a diuretic, or a laxative.

10. A method for detecting liver fibrosis in a subject, comprising the steps:
    measuring the subject's heartbeat rate;
    measuring the frequency of blood flow in at least two locations in a subject's liver using a Doppler Ultrasound system; and
    determining a shift in frequency of blood flow between the at least two locations in the liver;
    wherein the shift in frequency of blood flow between the at least two locations is an indication of the presence of liver fibrosis in the subject.

11. The method of claim 10, wherein the frequency of blood flow is measured by Doppler Ultrasound in at least three locations in the hepatic vein of the subject.

12. A method for treating or preventing liver fibrosis in a subject, comprising the steps:
    measuring the subject's heartbeat rate;
    measuring frequency of blood flow by Doppler Ultrasound in a portal vein of the subject;
    measuring frequency of blood flow by Doppler Ultrasound in a hepatic vein of the subject;
    determining the presence of a shift in the frequency of blood flow in the hepatic vein as compared to the frequency of blood flow in the portal vein; wherein an increase in the frequency of blood flow in the hepatic vein as compared to the frequency of blood flow in the portal vein is an indication of liver fibrosis; and
    administering a therapeutic agent, or therapeutic treatment, if the frequency of blood flow in the hepatic vein is increased as compared to the frequency of blood flow in the portal vein.

13. The method of claim 12, wherein the frequency of blood flow is measured by Doppler Ultrasound in at least two locations in the hepatic vein of the subject.

14. The method of claim 12, wherein the frequency of blood flow is measured by Doppler Ultrasound in three locations in the hepatic vein of the subject.

15. The method of claim 12, wherein the presence of a shift in the frequency of blood flow in the hepatic vein as compared to the frequency of blood flow in the portal vein of greater than about 0.0401 Hz is an indication of stage 4 liver fibrosis.

16. The method of claim 12, wherein the presence of a shift in the frequency of blood flow in the hepatic vein as compared to the frequency of blood flow in the portal vein of greater than about 0.0251 Hz and less than about 0.0401 Hz is an indication of stage 3 liver fibrosis.

17. The method of claim 12, wherein the presence of a shift in the frequency of blood flow in the hepatic vein as compared to the frequency of blood flow in the portal vein of greater than about 0.0200 Hz and less than about 0.0251 Hz is an indication of stage 2 liver fibrosis.

18. The method of claim 12, wherein the presence of a shift in the frequency of blood flow in the hepatic vein as compared to the frequency of blood flow in the portal vein of greater than about 0.0068 Hz and less than about 0.0200 Hz is an indication of stage 1 liver fibrosis.

19. The method of claim 12, wherein the therapeutic agent is selected from an antiviral agent, antibiotic, a diuretic, or a laxative.

20. The method of claim 12, wherein the therapeutic agent is administered for the prevention of the progression between stages of liver fibrosis.

\* \* \* \* \*